United States Patent [19]

Baum et al.

[11] 4,215,228

[45] Jul. 29, 1980

[54] 2-FLUORO-2-NITROPROPANEDIOL

[75] Inventors: Kurt Baum, Pasadena; Philip T. Berkowitz, Santa Ana, both of Calif.

[73] Assignee: The United States of America as represented by the Secretary of the Navy, Washington, D.C.

[21] Appl. No.: 933,365

[22] Filed: Aug. 14, 1978

[51] Int. Cl.² .............................................. C07C 79/16
[52] U.S. Cl. .................................................. 568/712
[58] Field of Search ........................................ 568/712

[56] References Cited

PUBLICATIONS

Eremenko et al, Chem. Abst., 70 (1969) 114510S.
Kirk–Othmer, Encyclopaedia of Chemical Technology, 2nd Ed. vol. 8, John Wiley & Sons, New York, 1965, pp. 581–583, 654–655.
Bowman, Chem. Abst., 78 (1973) 67523b.
Kissinger et al, Chem. Abst. 64 (1966) 731e.

Primary Examiner—Howard T. Mars
Attorney, Agent, or Firm—R. S. Sciascia; W. Thom Skeer; L. Ek. Pohl

[57] ABSTRACT

A novel process for preparing 2-fluoro-2-nitro-3-propanediol by reacting diethyl fluoronitromalonate with formaldehyde in the presence of an alkali metal hydroxide.

5 Claims, No Drawings

2-FLUORO-2-NITROPROPANEDIOL

BACKGROUND OF THE INVENTION

This invention relates to a process for the preparation of 2-fluoro-2-nitro-1,3-propanediol which is useful for formulation of explosives and propellants and as a precursor for the production of 3-fluoro-3-nitrooxetane and nitro polyethers.

2-Fluoro-2-nitro-1,3-propanediol has been prepared in low yields by fluorination of the cyclic ketal salt

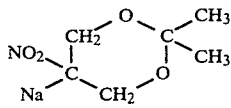

by L. W. Kissinger and T. M. Benziger and R. K. Rohner as reported in a book entitled "Nitro Compounds" which was put out by Tetrahedron (Vol. 20., Suppl. 1) in 1964. The article is entitled "The Action of polyphosphoric Acid on 2-Nitro-1,3-Propanediols and Some of Their Carbonate, Sulphite and 1,3-Dioxane Derivatives" and appears on p. 320 of the aforementioned book. The compound also may be prepared by fluorination of 2-sodium-2-nitro-1,3-propanediol in water or ethanol. The first method produces low yields and the second must be done slowly to prevent firing or charing. Both methods are impractical for large scale production.

Alternate possible methods of preparation would include aldol condensations of aldehydes with nitroalkanes as shown in U.S. Pat. Nos. 3,658,921 and 3,711,561 but this method appears to be impractical on a large scale.

SUMMARY OF THE INVENTION

The invention embodies the discovery that formaldehyde reacts with diethyl fluoronitromalonate in the presence of an alkali to give 2-fluoro-2-nitro-1,3-propanediol in satisfactory yields.

DESCRIPTION OF THE PREFERRED EMBODIMENT

The starting materials used are fluoronitromalonates produced by well known procedures involving fluorination of nitromalonate salts.

The fluoronitromalonates are reacted with a source of formaldehyde which can be a solution of formaldehyde or para formaldehyde. The reaction is conducted in the presence of alkali metal hydroxides, both sodium and potassium hydroxide were used and found satisfactory.

The reaction is preferably conducted at temperatures of from 10° C. to −10° C. The product is separated by conventional separation means.

Reaction times will vary from 1 hour to 1 day depending on reaction conditions.

While the Examples describe the invention on a batch basis, it may, of course be practical on a continuous basis with continuous addition of starting materials, continuous removal of products, and with recycle of unreacted materials back into the reactor.

The following examples will serve to illustrate the process of this invention, it being clearly understood, however, that the conditions of the reactions described therein are by no means intended to limit the scope of this invention.

EXAMPLE I

A suspension of 89.2 g (0.40 mole) of diethyl fluoronitromalonate in 80 ml (1.0 mole) of 37% aqueous formaldehyde was cooled in an ice-bath to 2° C. A solution of 66.0 g (1.60 mole) of sodium hydroxide in 400 ml of water was then added dropwise with vigorous stirring over 100 minutes, below 10° C. After the reaction mixture was stirred overnight in the ice-bath, it was filtered and the filtrate was extracted with ethyl acetate ($3 \times 1000$ ml). The ethyl acetate solution was dried over sodium sulfate and distilled (0.17 mm/170° bath) to give 25.5 g (45.9%) of 2-fluoro-2-nitro-1,3-propanediol; mp 86°–87° C.; $^1$HNMR (acetone-$d_6$) $\delta 3.90$ (d, J=6Hz, 2 H, —CH$_2$—), 4.20 (t, J=6Hz, 2 H, —CH$_2$—), 4.80 (t, J=6Hz, 2 H, —OH); $^{19}$FNMR (acetone-$d_6$) $\phi 145.6$ (quintuplet J=16Hz). IR (CH$_2$Cl$_2$) 3620 (—OH), 1575, 1335 (—NO$_2$), 1040 cm$^{-1}$ (C=F).

EXAMPLE II

To a suspension of 24.5 g (0.11 mol) diethyl fluoronitromalonate and 8.8 g (0.275 mol) of paraformaldehyde in 110 ml of methanol, at −9° C., was added 7.28 (0.11 mol) of potassium hydroxide in 55 ml of methanol dropwise over 27 minutes. After 45 minutes, the reaction temperature was raised to 0°. No precipitate remained after 1 hour. The reaction mixture was diluted with 330 ml of water and the pH was adjusted to 5 with concentrated hydrochloric acid. The reaction mixture was saturated with sodium chloride and extracted with ethyl acetate ($3 \times 275$ ml). The ethyl acetate solution was dried and stripped. Toluene was twice added and removed in vacuo to leave 12.3 g of semi-solid residue. Vacuum distillation gave 6.99 g (45.7%) of 2-fluoro-2-nitro-1,3-propanediol.

While there has been described in the foregoing what may be considered to be preferred embodiments of the invention, modifications may be made therein without departing from the concepts of the invention, and it is intended to cover all such as fall within the scope of the appended claims.

What is claimed is:

1. A process for the production of 2-fluoro-2-nitropropanediol comprised of the steps of:
   combining diethyl fluronitromalonate with a compound selected from the group of formaldehyde solutions and paraformaldehyde, in the presence of an alkali metal hydroxide between 10° and −10° C. and separation of the product.

2. The process of claim 1 wherein the alkali metal hydroxide is potassium hydroxide.

3. The process of claim 2 wherein the alkali metal hydroxide is sodium hydroxide.

4. The process of claim 1 where the product is separated by filtration, extraction with a solvent and distillation.

5. The process of claim 4 wherein the solvent is ethyl acetate.